United States Patent [19]

Buese

[11] Patent Number: 4,826,710
[45] Date of Patent: May 2, 1989

[54] BISCYCLOSILOXANE IMIDES, METHOD OF MAKING AND USE

[75] Inventor: Mark A. Buese, Upper Darby, Pa.

[73] Assignee: General Electric Company, Schenectady, N.Y.

[21] Appl. No.: 191,638

[22] Filed: May 9, 1988

[51] Int. Cl.$^4$ .......................... B05D 3/02; B32B 9/04; C07F 7/02

[52] U.S. Cl. .................................... 427/387; 428/447; 548/406

[58] Field of Search ....................... 427/387; 428/447; 548/406

[56] References Cited

U.S. PATENT DOCUMENTS 4,730,055  3/1988  Rich ..................................... 548/406
4,780,501 10/1988  Rich ................................. 548/406 X

OTHER PUBLICATIONS

*Journal of Polymer Science,* vol. Xi, Gilbert et al., "Transient Catalysts for the Polymerization of Organosiloxanes", (1959), pp. 35–58.

*Primary Examiner*—Michael Lusignan
*Attorney, Agent, or Firm*—William A. Teoli; James C. Davis, Jr.; James Magee, Jr.

[57] ABSTRACT

Biscyclosiloxane imides such as 1,3-bis[5'-(heptamethylcyclotetrasiloxyl)-bicyclo[2.2.1]heptane-2',3'-dicarboxylicimido]phenylene are made by intercondensing the corresponding cyclicsiloxane norbornane anhydride with aromatic diamine. The biscylosiloxane imides can be converted to coating compositions or elastomers.

6 Claims, No Drawings

BISCYCLOSILOXANE IMIDES, METHOD OF MAKING AND USE

BACKGROUND OF THE INVENTION

The present invention relates to certain biscyclosiloxane imides such as 1,3-bis[5'-(heptamethylcyclotetrasiloxyl)-bicyclo[2.2.1]heptane-2',3'-dicarboxylicimido]phenylene. The conversion of the aforementioned biscyclosiloxane imide to more flexible resins by the use of an acid catalyst is also provided.

Prior to the present invention, biscyclosiloxanes, made by the hydrosilylation of vinyl-heptamethylcyclotetrasiloxane with 1,1,3,3-tetramethyldisiloxane, was shown by A. A. Zhdanov, V. M. Kotov et al., Izv. Akad. Nauk SSSR, Ser. Kim 1984. Bicyclosiloxanes to prepare networks has been reported by A. R. Gilbert et al., *Journal of Polymer Science*, 1959, 40,35. Ryang U.S. Pat. Nos. 4,381,396 and 4,472,565 assigned to the same assignee as the present invention and incorporated herein by reference, show the preparation of 5-(heptamethylcyclotetrasiloxyl)-bicyclo[2.2.1]heptane-2,3-dicarboxylic anhydride and its use in making silicone-polyimide copolymers.

The present invention is based on the discovery, that a cyclosiloxane anhydride of the formula

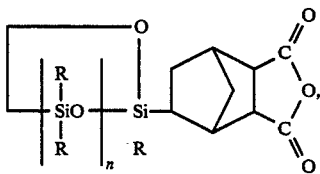

where R is a $C_{(1-14)}$ monovalent hydrocarbon radical or a $C_{(1-14)}$ monovalent hydrocarbon radical substituted with radicals inert during equilibration, and n is an integer having a value of 2 to 10 inclusive, can be made by the hydrosilylation of a bicyclo[2.2.1]heptane-2,3-dicarboxylic anhydride with a mixture of cyclic siloxanes containing chemically combined diorganosiloxy units and organosiloxy units having hydrogen attached to silicon followed by fractional distillation to recover the desired cyclosiloxane anhydride. The cyclosiloxane anhydride of Formula (1) can thereafter be reacted with an organic diamine, such as metaphenylene diamine, to produce the desired biscyclosiloxane imide.

STATEMENT OF THE INVENTION

There is provided by the present invention, biscyclosiloxane imides included within the formula

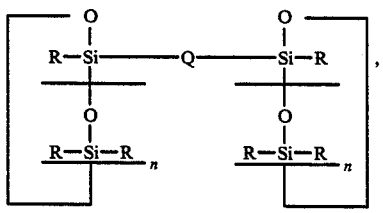

where R and n have been previously defined, Q is a divalent group having the formula

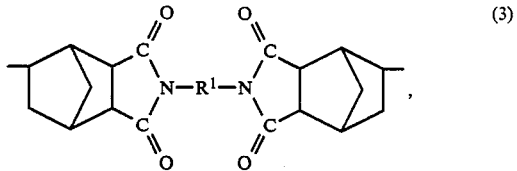

$R^1$ is a divalent $C_{(6-14)}$ aromatic hydrocarbon radical or a $C_{(6-14)}$ aromatic hydrocarbon radical substituted with radicals inert during equilibration Monovalent radicals which are included by R in Formulas (1) and (2) are, for example, alkyl radicals such as methyl, ethyl, propyl, butyl, pentyl, hexyl, heptyl; haloalkyl radicals such as trifluoropropyl; cyanoalkyl radicals such as cyanoethyl and cyanopropyl; alkenyl radicals such as vinyl and allyl; aryl radicals such as phenyl, tolyl, xylyl and naphthyl; substituted aryl radicals such as chlorophenyl, bromotolyl and nitrophenyl. Divalent aromatic radicals included within $R^1$ are, for example, phenylene, toluene, naphthalene, halophenylene and nitrotoluene.

Some of the aryldiamines which can be utilized in the practice of the invention to make the biscyclosiloxane imides are, for example, o-phenylenediamine; m-phenylenediamine; p-phenylenediamine; 4,4'-diaminodiphenylpropane; 4,4'-diaminodiphenylmethane (commonly named 4,4'-methylenedianiline); 4,4'-diaminodiphenyl sulfide (commonly named 4,4'-thiodianiline); 4,4'-diaminodiphenyl ether (commonly named 4,4'-oxydianiline); 1,5-diaminonaphthalene; 3,3'-dimethylbenzidine; 3,3'-dimethoxybenzidine; 2,4-bis(β-amino-t-butyl)toluene; 1,3-diamino-4-isopropylbenzene; 1,2-bis(3-aminopropoxy)ethane; benzidine; m-xylylenediamine; p-xylylenediamine; 2,4-diaminotoluene; and 2,6-diaminotoluene.

In the practice of the invention, the preparation of the cyclosiloxane anhydride of Formula (1) can be carried out by the hydrosilylation of 5-norbornene-2,3-dicarboxylic acid anhydride referred to hereinafter as "norbornene anhydride" with a mixture of cyclic siloxanes, for example, cyclic siloxanes consisting of chemically combined dimethylsiloxy units and methylsiloxy units employing an effective amount of a platinum catalyst. Suitable hydrosilylation catalysts which can be used are, for example, shown by Karstead, U.S. Pat. No. 3,775,442, Ashby, U.S. Pat. No. 3,159,601 and Lamoreaux, U.S. Pat. No. 3,220,972. An effective amount of a platinum catalyst is about 0.001% to 0.1% by weight of platinum based on the weight of the hydrosilylation mixture. Alternatively, the cyclosiloxane anhydride of Formula (1) can be prepared by the hydrosilylation of norbornene anhydride using a pure cyclic siloxane containing only one SiH group or by the hydrosilylation of a linear or cyclosiloxane fluid containing multiple SiH groups. The resulting addition products can be followed by acid catalyzed equilibration. There can be used additional cyclic siloxanes, such as hexamethylcyclotrisiloxane or octamethylcyclotetrasiloxane, or a polydimethylsiloxane fluid. After quenching of the acid, the equilibration mixture can be concentrated and the desired monoanhydride cyclo siloxane can be isolated by fractional distillation.

The siloxane imides of Formula (2) can be prepared by effecting reaction between the siloxane anhydride of Formula (1) and an appropriate aryldiamine such as 1,3-phenylenediamine. The mixture can be agitated and heated to a temperature of up to 175° C. in the presence of a condensation catalyst, such as a dialkylaminopyridine. The desired bicyclosiloxane imide can be recovered by applying a vacuum to the mixture. The final product can be recrystallized in accordance with standard techniques such as recrystallization from a suitable organic solvent.

The bicyclosiloxane imides of the present invention can be directly cured to a hard network utilizing an effective amount of a acid catalyst such as trifluoromethanesulfonic acid. An effective amount of equilibration catalyst is 0.0001% to 5% based on the weight of resin. Additional equilibration catalysts which can be used are, for example, methane sulfuric acid, acid treated clay, etc. The polymerization of the bicyclosiloxane imide can be effected at temperature of 25° C. to 100° C. in the presence of an organic solvent, or in the melt. Suitable organic solvents include, for example, dichloromethane and toluene. If desired, the biscyclosiloxane imides can be further equilibrated with a cyclic siloxane, such as octamethylcyclotetrasiloxane to effect the formation of a more flexible network.

The following examples are given by way of illustration and not by way of limitation. All parts are by weight.

EXAMPLE

There was stirred at a temperature of 75° C., a mixture of 21.31 grams of cyclic siloxanes having a ratio of dimethylsiloxy units to methylsiloxy units of 3:1 (providing 146 millimoles of ≡SiH), where and most of the mixture was heptamethylcyclotetrasiloxane, 20 grams of 5-norbornene-2,3-dicarboxylic acid anhydride and 40 microliters of a 5% solution of a vinyl siloxane platinum (32 ppm. Pt) as shown by U.S. Pat. No. 3,775,442. After a 20 minute induction period, the mixture exothermed and become homogeneous. An alliquot of the mixture was removed after a total of 50 minutes which indicated the complete conversion of the starting olefin. The desired product was distilled from the mixture of 145° C., 0.25 torr. There was obtained a yield of 40.28 grams (74%) of 5-(heptamethylcyclotetrasiloxy)-bicyclo[2.2.1]heptane-2,3dicarboxylic anhydride. The product had a melting point of 55°-58° C. and its identity was further confirmed by gas chromatographic and NMR analysis.

A mixture of 20.00 grams (45 millimoles) of the above cyclosiloxane anhydride, 2.45 grams (23 millimoles) of 1,3-phenylenediamine and 0.06 grams of 4-N,N-dimethylaminopyridine. The mixture was stirred mechanically and warmed to 160° C. with the rapid evolution of water. After a period of about 25 minutes, a vacuum was applied to the mixture. When the mixture stopped bubbling, an alliquot was removed for GC analysis. There was obtained a 98% yield of the desired product. Based on method of preparation and NMR and IR spectroscopy, the product was 1,3-bis-[5'-(heptamethylcyclotetrasiloxyl)-bicyclo[2.2.1]heptane-2',3'-dicarboxylicimido]phenylene.

A solution of 5.5 grams (7.3 millimoles) of the above bissiloxane imide in 10 ml. of dichloromethane was dried over calcium hydride and filtered using a 5 micron Millipore filter. One third of the resulting solution was agitated with 15 microliters of trifluoromethanesulfonic acid in a sealed polyethylene container. After 10 minutes the mixture did not flow. The methylene chloride was allowed to evaporated leaving a strong, hard, colorless insoluble and transparent resin. The resin was found to be suitable as a hardcoat composition when applied onto a suitable substrate such as an aluminum, steel or silicon substrate.

The above procedure was repeated except that there was added 1.2 mole (4.9 millimoles) of octamethylcyclotetrasiloxane with the biscyclosiloxane imide and trifluoromethanesulfonic acid. After the mixture was agitated for 10 minutes in a sealed polyethylene container it did not flow. Methylene chloride was then allowed to evaporate from the resulting mass. There was obtained a strong, flexible, colorless insoluble transparent resin which was useful as a flexible coating composition or as a high strength elastomer.

Although the above example is directed to only a few of the very many variables which can be utilized in the practice of the present invention, it should be understood that the present invention is directed to a much broader variety of bicyclosiloxane imides as shown in the description preceding the example.

What is claimed and sought to be protected by Letters Patent of the United States is as follows:

1. A biscyclosiloxaneimide having the formula,

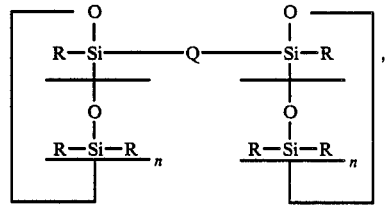

where Q is

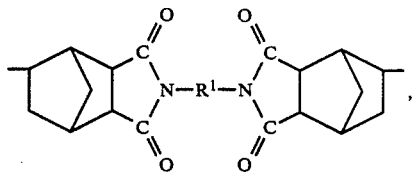

R is a monovalent hydrocarbon radical or monovalent hydrocarbon radical substituted with radicals inert during equilibration, $R^1$ is a divalent $C_{(6-14)}$ aromatic hydrocarbon radical or a $C_{(6-14)}$ aromatic hydrocarbon radical substituted with radicals inert during equilibration, and n is an integer having a value of 2 to 10 inclusive.

2. Biscyclosiloxaneimide in accordance with claim 1, where $R^1$ is phenylene.

3. A method of coating a substrate with a siloxaneimide which comprises,
 (1) agitating a fluid mixture comprising by weight
  (A) 100 parts of a biscyclosiloxaneimide of the formula,

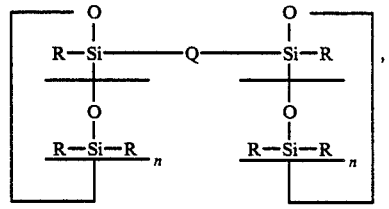

(B) up to 200 parts of a cyclic polydiorganosiloxane, and
 (C) an effective amount of an equilibration catalyst (2) applying the equilibrated mixture of (1) onto a substrate where Q is

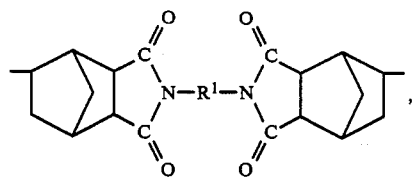

R is a monovalent hydrocarbon radical or monovalent hydrocarbon radical substituted with radicals inert during equilibration, $R^1$ is a divalent $C_{(6-14)}$ aromatic hydrocarbon radical or a $C_{(6-14)}$ aromatic hydrocarbon radical substituted with radicals inert during equilibration, and n is an integer having a value of 2 to 10 inclusive.

4. A coating method in accordance with claim 3, where the fluid mixture contains an organic solvent.

5. A coating method in accordance with claim 3, where the fluid mixture is in the melt.

6. A coating method in accordance with claim 3, where the equilibration catalyst is trifluoromethanesulfonic acid.

* * * * *